(12) United States Patent
Bauman et al.

(10) Patent No.: US 9,682,830 B2
(45) Date of Patent: Jun. 20, 2017

(54) APPARATUSES FOR TRANSFERRING ARTICLES AND METHODS OF MAKING THE SAME

(71) Applicant: The Procter & Gamble Company, Cincinnati, OH (US)

(72) Inventors: Bryan Wesley Bauman, Cincinnati, OH (US); Scott Alan King, Liberty Township, OH (US); Jennifer Lynn Tuertscher, Cincinnati, OH (US); Andrew MacGee, Oxford, OH (US); Markus Grädler, Bayern (DE); Christian Hans Günther Fuchs, Heilsbronn (DE)

(73) Assignee: The Procter & Gamble Company, Cincinnati, OH (US)

( * ) Notice: Subject to any disclaimer, the term of this patent is extended or adjusted under 35 U.S.C. 154(b) by 212 days.

(21) Appl. No.: 14/588,469

(22) Filed: Jan. 2, 2015

(65) Prior Publication Data
US 2016/0194163 A1 Jul. 7, 2016

(51) Int. Cl.
*B65G 47/82* (2006.01)
*A61F 13/15* (2006.01)
*B65H 29/24* (2006.01)

(52) U.S. Cl.
CPC ........ *B65G 47/82* (2013.01); *A61F 13/15577* (2013.01); *B65H 29/241* (2013.01);
(Continued)

(58) Field of Classification Search
CPC . A61F 13/15577; B65G 47/82; B65H 29/241; B65H 2301/4472; B65H 2406/345; B65H 2801/57; B65H 2513/108
See application file for complete search history.

(56) References Cited

U.S. PATENT DOCUMENTS

| 4,333,790 A | 6/1982 | Schaffron |
| 4,429,781 A | 2/1984 | Holzhauser |

(Continued)

FOREIGN PATENT DOCUMENTS

| CH | 678616 | 10/1991 |
| EP | 0812789 | 12/1997 |

(Continued)

OTHER PUBLICATIONS

Michael C. Niu; Composite Airframe Structures; Practical Design Information and Data; Dec. 31, 1992; pp. 383-392.*

(Continued)

*Primary Examiner* — Jacob Cigna
*Assistant Examiner* — Lee A Holly
(74) *Attorney, Agent, or Firm* — Christian M. Best

(57) ABSTRACT

A method of manufacturing a transfer assembly for transferring articles from a first moving carrier to a second moving carrier is provided. The method comprises providing a programmable motor and a motor control system. The motor control system and the programmable motor define an excitation frequency. The method comprises providing a carrier member comprising a housing comprising a wall and shifting a natural frequency of the carrier member by forming the wall with a first carbon fiber layer having a first fiber orientation extending in a first direction and with a second carbon fiber layer having a second fiber orientation extending in a second direction that is different than the first direction. The shifting the natural frequency establishes the natural frequency of the carrier member to be at least 1.1 times greater than or at least 1.1 times less than the excitation frequency.

20 Claims, 13 Drawing Sheets

(52) U.S. Cl.
CPC .............. *B65H 2301/4472* (2013.01); *B65H 2406/345* (2013.01); *B65H 2513/108* (2013.01); *B65H 2801/57* (2013.01)

(56) References Cited

U.S. PATENT DOCUMENTS

| | | | |
|---|---|---|---|
| 4,726,876 A | 2/1988 | Tomsovic, Jr. | |
| 5,091,039 A | 2/1992 | Ujimoto et al. | |
| 5,235,515 A | 8/1993 | Ungpiyakul et al. | |
| 5,556,504 A | 9/1996 | Rajala et al. | |
| 5,684,344 A | 11/1997 | Takei | |
| 5,693,165 A | 12/1997 | Schmitz | |
| 5,693,195 A | 12/1997 | Saito et al. | |
| 5,766,406 A | 6/1998 | Bohn et al. | |
| 5,776,289 A | 7/1998 | Steidinger | |
| 5,888,343 A | 3/1999 | Olson | |
| 5,895,555 A | 4/1999 | Van Den Bergh | |
| 5,965,963 A | 10/1999 | Chitayat | |
| 5,994,798 A | 11/1999 | Chitayat | |
| 6,022,443 A | 2/2000 | Rajala et al. | |
| 6,086,694 A | 7/2000 | Winter et al. | |
| 6,149,755 A | 11/2000 | McNichols et al. | |
| 6,165,306 A | 12/2000 | Rajala | |
| 6,450,321 B1* | 9/2002 | Blumenthal | A61F 13/15764 156/520 |
| 6,705,453 B2 | 3/2004 | Blumenthal et al. | |
| 6,814,217 B2 | 11/2004 | Blumenthal et al. | |
| 6,942,086 B2 | 9/2005 | Bridges et al. | |
| 7,811,403 B2 | 10/2010 | Andrews et al. | |
| 8,100,253 B2 | 1/2012 | Walsh et al. | |
| 9,227,794 B2 | 1/2016 | Papsdorf et al. | |
| 2003/0079330 A1 | 5/2003 | Stopher et al. | |
| 2003/0121614 A1 | 7/2003 | Tabor et al. | |
| 2005/0145322 A1 | 7/2005 | Hoffman et al. | |
| 2013/0270065 A1* | 10/2013 | Papsdorf | A61F 13/15764 198/377.01 |
| 2013/0270066 A1 | 10/2013 | Papsdorf et al. | |
| 2013/0305511 A1 | 11/2013 | Schoultz et al. | |
| 2014/0110052 A1 | 4/2014 | Findley et al. | |
| 2014/0110226 A1 | 4/2014 | Findley et al. | |
| 2014/0170369 A1* | 6/2014 | Bech | B32B 3/02 428/113 |
| 2014/0174883 A1 | 6/2014 | Papsdorf et al. | |

FOREIGN PATENT DOCUMENTS

| | | |
|---|---|---|
| JP | 2001025285 | 1/2001 |
| WO | WO-9519752 | 7/1995 |

OTHER PUBLICATIONS

International Search Report and Written Opinion, PCT/US2015/067981, date of mailing Apr. 12, 2016.

All Office Actions, Responses and Claims, U.S. Appl. No. 14/588,464.

All Office Actions, Responses and Claims, U.S. Appl. No. 14/588,478.

* cited by examiner

APPARATUSES FOR TRANSFERRING ARTICLES AND METHODS OF MAKING THE SAME

FIELD

The present disclosure is generally directed to apparatuses for transferring articles and methods or making the same and, is more particularly directed to apparatuses for transferring articles from a first carrier moving at a first speed to a second carrier moving at a second speed and methods of making the same.

BACKGROUND

Disposable absorbent articles, such as disposable diapers, generally have been manufactured by a process where articles, discrete articles, or components of different materials, such as leg elastics, waist elastics, ears, tapes, fasteners, or other components have been applied to a substrate (e.g., a chassis of a diaper or a web of chassis material) supported on a continuously moving carrier. Often, the speed at which the articles are fed into the process on a carrier is not the same as the speed of the continuously moving carrier conveying the substrate. Thus, the speed of the articles must be changed, using a transfer apparatus, to match the speed of the continuously moving carrier to properly apply the articles to the substrate without adversely affecting the process or the finished product.

Similarly, labels or stickers are typically placed onto a moving substrate when the speed at which the labels or stickers are fed into the process is not the same as the speed of the moving substrate to be labeled or stickered. Thus, the speed of the labels or stickers must be changed, using a transfer apparatus, to match the speed of the moving substrate to properly apply the labels or stickers to the substrate without adversely affecting the process or the finished product.

Transfer apparatuses for the articles may generally comprise a motor and a carrier member operably engaged with the motor. The carrier member comprises a housing having an outer surface configured to receive one or more of the articles to be transferred. The housing is rotated by the motor such that the outer surface receives the article from a first moving carrier in a receiving zone and deposits the article onto a substrate being conveyed by a second moving carrier in an application zone. Considering that the speed of the first and second moving carriers is typically different, the carrier member is typically rotated at a variable rate of speed to account for the different speeds of the first and second moving carriers.

The motors of the transfer apparatuses are typically operably linked to a motor control system that causes the motor to vary the speed of rotation of the housing. The motor control system and the motor define an excitation frequency. The excitation frequency may coincide with the natural frequency of certain materials of the carrier member or other components of the transfer apparatus, for example carbon fiber materials. This coincidence may cause the carbon fiber or other materials to crack. As such, carbon fiber or other materials subject to cracking have not previously been used as a material of a carrier member because of this coincidence, but would be desirable to use because of their high strength and light weight. What is needed are apparatuses that use carbon fiber, or other materials typically subject to cracking, in at least portions of carrier members without coincidence between an excitation frequency of a motor control system and motor and a natural frequency of the carbon fiber or other materials subject to cracking and methods for making the same.

SUMMARY

To resolve the above described problem in regard to using carbon fiber or other materials subject to cracking as a material in a portion of a transfer apparatus (e.g., as a portion of a carrier member), the present disclosure is directed, in part, to apparatuses for transferring one or more articles from a first carrier moving at a first speed to a second carrier moving at a second, different speed, wherein the transfer apparatus may comprise a carrier member having a housing comprising carbon fiber, layers of carbon fiber, and/or carbon fiber composites (herein together sometimes referred to as "carbon fiber"). The present disclosure also comprises methods for making the apparatuses. The transfer apparatus may also comprise a motor configured to drive the carrier member and a motor control system operably linked to the motor and configured to vary the speed of the motor. The motor control system may comprise an amplifier and/or a controller. Carbon fiber is able to be used in the context of the present disclosure in view of the specific layering of the carbon fiber to cause all natural frequencies of the carbon fiber to be shifted at least 1.1 times away from all excitation frequencies of the motor control system and the motor. Without the teachings of the present disclosure, the carbon fiber tends to crack when at least one excitation frequency of the motor control system and the motor coincides with at least one natural frequency of the carbon fiber.

In a form, the present disclosure is directed, in part, to an apparatus for transferring one or more articles from a first carrier moving at a first speed to a second carrier moving at a second speed that is different than the first speed. The apparatus comprises a programmable motor and a carrier member operably engaged with the programmable motor. The carrier member comprises a housing comprising a wall and an outer surface configured to receive the one or more articles from the first moving carrier in a receiving zone and configured to deposit the one or more articles onto the second moving carrier in an application zone. The wall comprises carbon fiber. The programmable motor is configured to move the outer surface of the housing at a third speed through the receiving zone and at a fourth speed through the application zone.

In a form, the present disclosure is directed, in part, to an apparatus for transferring one or more articles from a first moving carrier to a second moving carrier. The apparatus comprises a first programmable motor, a second programmable motor, a first carrier member operably engaged with the first programmable motor, and a second carrier member operably engaged with the second programmable motor. The first programmable motor is configured to rotate the first carrier member in an orbital path. The first carrier member comprises a housing comprising a wall and an outer surface configured to receive the one or more articles from the first moving carrier in a receiving zone and configured to deposit the one or more articles onto the second moving carrier in an application zone. The wall comprises carbon fiber. The second programmable motor is configured to rotate the second carrier member in the orbital path. The second carrier member comprises a housing comprising a wall and an outer surface configured to receive the one or more articles from the first moving carrier in the receiving zone and configured to deposit the one or more articles onto the second moving carrier in the application zone. The wall comprises carbon fiber. The first and second carrier members are located at least partially between the first and second programmable motors.

In a form, the present disclosure is directed, in part, to an apparatus for transferring one or more articles from a first moving carrier to a second moving carrier. The apparatus comprises a first motor, a second motor, a first transfer member operably engaged with the first motor, and a second transfer member operably engaged with the second motor. The first and second transfer members are generally aligned with respect to a common axis. The apparatus comprises a first carrier member engaged with the first transfer member. The first transfer member is configured to guide the first carrier member in an orbital path. The first carrier member comprises a housing comprising a wall and an outer surface configured to receive the one or more articles from the first carrier in a receiving zone and configured to deposit the one or more articles onto the second moving carrier in an application zone. The wall comprises carbon fiber. The apparatus comprises a second carrier member engaged with the second transfer member. The second transfer member is configured to guide the second carrier member in the orbital path. The second carrier member comprises a housing comprising a wall and an outer surface configured to receive the one or more articles from the first moving carrier in the receiving zone and configured to deposit the one or more articles onto the second moving carrier in the application zone. The wall comprises carbon fiber.

In a form, the present disclosure is directed, in part, to a method of manufacturing a transfer assembly configured to transfer one or more articles from a first moving carrier to a second moving carrier. The method comprises providing a programmable motor and a motor control system for the programmable motor. The motor control system and the programmable motor define at least one excitation frequency. The method comprises providing a carrier member comprising a housing comprising a carbon fiber portion and shifting at least one natural frequency of the carrier member by forming the carbon fiber portion with a first carbon fiber layer having a first fiber orientation extending in a first direction and with a second carbon fiber layer having a second fiber orientation extending in a second direction that is different than the first direction. The shifting the natural frequency step establishes the at least one natural frequency of the carrier member to be at least 1.1 times greater than or at least 1.1 times less than the at least one excitation frequency of the motor control system and the programmable motor.

In a form, the present disclosure is directed, in part, to a method of shifting a natural frequency of a carrier member comprising a housing comprising a wall. The carrier member is configured to be rotated about an axis of rotation by a programmable motor in communication with a motor control system such that the carrier member is configured to transfer one or more articles from a first moving carrier to a second moving carrier. The motor control system and the programmable motor have a plurality of excitation frequencies. The method comprises forming the wall of the housing of the carrier member. The forming step comprises placing a first carbon fiber layer having a first fiber orientation extending in a first direction and placing a second carbon fiber layer on a first side of the first layer. The second carbon fiber layer has a second fiber orientation extending in a second direction that is different than the first direction. The method comprises placing a third carbon fiber layer on a second side of the first layer. The third carbon fiber layer has a third fiber orientation extending generally in the second direction such that the plurality of excitation frequencies of the motor control system and the programmable motor do not interfere with the natural frequency of the carrier member.

In a form, the present disclosure is directed, in part, to a method of forming a wall of a housing of a carrier member. The housing defines a longitudinal axis. The carrier member has a natural frequency that is at least 1.1 times greater than or at least 1.1 times less than an excitation frequency of a programmable motor and a motor control system for the programmable motor. The carrier member is configured to transfer an article from a first moving carrier to a second moving carrier. The programmable motor is configured to rotate the carrier member about an axis of rotation. The method comprises applying a first carbon fiber layer. The first carbon fiber layer has a first fiber orientation extending in the range of −40 to −20 degrees from the longitudinal axis. The method comprises applying a second carbon fiber layer. The second carbon fiber layer has a second fiber orientation extending in the range of −40 to −20 degrees from the longitudinal axis. The first and second carbon fiber layers together form the wall.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting forms of the disclosure taken in conjunction with the accompanying drawings, wherein.

DETAILED DESCRIPTION

Figure 1:
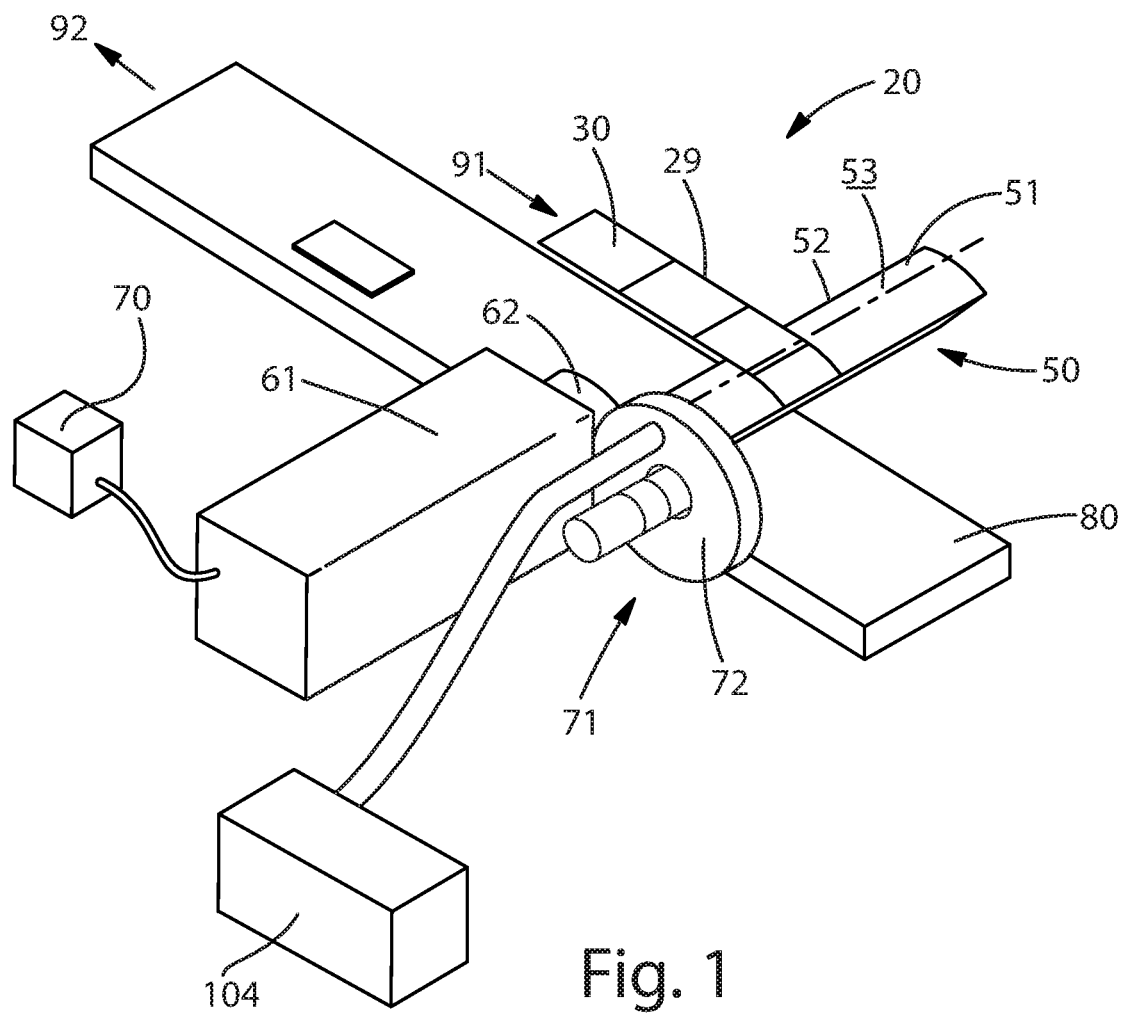
FIG. 1 is a perspective view of an example transfer apparatus used to transfer one or more articles from a first carrier moving at a first speed to a second carrier moving at a second speed in accordance with the present disclosure.

Various non-limiting forms of the present disclosure will now be described to provide an overall understanding of the principles of the structure, function, manufacture, and use of the apparatuses for transferring articles and methods for making the same disclosed herein. One or more examples of these non-limiting forms are illustrated in the accompanying drawings. Those of ordinary skill in the art will understand that the apparatuses for transferring articles and methods for making the same described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

DEFINITIONS

As used herein, the term "absorbent article" refers to disposable devices such as infant, child, or adult incontinence diapers, training pants, incontinence pants, sanitary napkins, and the like which are placed against or in proximity to the body of the wearer to absorb and contain the various exudates discharged from the body (e.g., menses, runny BM, and urine). Typically, these articles comprise a topsheet, backsheet, an absorbent core, optionally an acquisition system (which may be comprised of one or several layers), and typically other components, with the absorbent core normally placed at least partially between the backsheet and the acquisition system or between the topsheet and the backsheet. The absorbent articles may take on any suitable configuration.

As used herein, the term "machine direction" is used herein to refer to the primary direction of material or web flow through a process or manufacturing line.

As used herein, the term "cross machine direction" or "cross machine directional" is used herein to refer to a direction that is generally perpendicular to, or perpendicular to, the machine direction.

The present disclosure provides apparatuses for receiving articles or discrete articles from a first moving carrier traveling at a first speed and applying the articles to a substrate (e.g., absorbent article chassis) on a second moving carrier traveling at a second speed. The present disclosure also provides methods for making the same. The apparatuses are particularly useful for applying any article or component to a substrate useful in the making of disposable absorbent articles and/or for placing labels or stickers onto any suitable articles or substrates. Those of skill in the art will recognize that the apparatuses of the present disclosure may also be used for applying any suitable article to any suitable substrate, component, web, or other material being conveyed by a moving carrier. As additional non-limiting examples, the articles being transferred by the apparatus of the present disclosure may be pads, wipes, towels, cellulosic materials, nonwoven materials, tow materials, cleaning substrates, polishing substrates, and/or scrubbing substrates.

Figure 2:
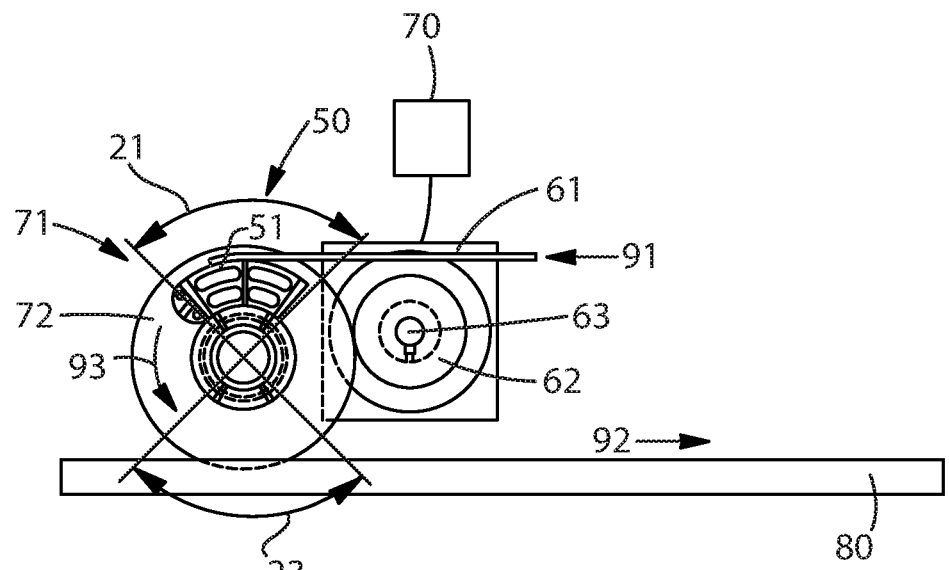
FIG. 2 is a schematic side view of the transfer apparatus of FIG. 1, in accordance with the present disclosure.

Referring to FIGS. 1 and 2, an example transfer apparatus is illustrated. The transfer apparatus 20 may receive discrete articles 30 traveling on a first moving carrier 29 moving at a first speed in the direction indicated by arrow 91 and may apply the articles 30 to a second moving carrier 80 traveling at a second speed in the direction indicated by arrow 92. The transfer apparatus 20 may comprise a motor 61 for transmitting rotational energy to a transfer member 71. The motor 61 may be operably linked or operably engaged with the transfer member 71 using any technique known to those skilled in the art such as, for example, a gear to gear connection, transmission belting and pulleys, gearboxes, direct couplings, and the like or any combinations thereof. For example, in FIG. 1 the transfer member 71 may comprise a driven gear 72 that is connected to a driving gear 62, which transmits rotational energy to the driven gear 72. In use, the driving gear 62 may engage and rotate the driven gear 72 which, in turn, may rotate a carrier member 50 of the transfer apparatus 20.

The illustrated example of the carrier member 50 comprises at least one housing 51 operably connected to the transfer member 71. In some instances, the transfer member 71 may form a portion of the carrier member 50. In such an instance, the transfer member 71 may be positioned more proximal to the motor 61 than the carrier member 50. The housing 51 may comprise a wall 52 and an outer surface 53. The wall 52 may comprise one or more layers of carbon fiber. In some configurations, the outer surface 53 may also comprise carbon fiber. The housing 51 of the carrier member 50 may be connected to the transfer member 71 by any technique known to those skilled in the art such as, for example, bolts, screws, pins, keys and matching key ways, connector parts such as shafting or brackets, adhesive bonding or gluing, welding and the like or combinations thereof. For instance, the housing 51 shown in FIG. 1 may be connected directly to the driven gear 72 by fitting the end of the housing 51 into a mating hole in the driven gear 72 and locking it into position with a pin. Similarly, other components of the transfer apparatus 20 may be connected together employing the above described assembly techniques.

The dimensions of the housing 51 may vary depending upon the desired output of the transfer apparatus 20 and the size and shape of the articles 30 being transferred. The housing 51 may comprise a crescent-shaped member having an outer, peripheral arc length spanning from about 5 degrees to about 355 degrees, an outer radius ranging from about 10 mm to about 1,000 mm or about 25 mm to about 500 mm, and a width ranging from about 25 mm to about 1,000 mm or about 50 mm to about 750 mm, specifically reciting all 0.1 increments within the above-specified ranges and all ranges formed therein or thereby. Other suitable dimensions are also within the scope of the present disclosure. As the transfer member 71 rotates, the carrier member 50 may travel in the direction indicated by arrow 93 as shown in FIG. 2. The circumferential, outer peripheral surface of the housing 51 defined by an outer radius may travel along and define an orbital path that passes through a receiving zone 21 and an application zone 23. The receiving zone 21 and the application zone 23 are defined by the respective regions of the orbital path traveled by the housing 51. The receiving zone and the application zone may be otherwise situated as well, as will be recognized by those of skill in the art.

The first moving carrier 29 may be moving at a first speed through the receiving zone 21 and the second moving carrier 80 may be moving at a second speed through the application zone 23. The motor 61 may be configured to move the outer surface 53 of the housing 21 at a third speed through or in the receiving zone 21 and at a fourth speed through or in the application zone 23. The first speed may be equal to, or substantially equal to, the third speed and the second speed may be equal to, or substantially equal to, the fourth speed to effectuate proper controlled transfer of the articles 30.

One illustrated example of the motor 61 comprises a rotatable circular driving gear 62 connected to an input shaft 63. In this example, the input shaft 63 is the output shaft of the motor 61. The transfer member 71 is placed parallel to the motor 61 such that the driving gear 62 meshes with the driven gear 72 using gear set-ups known to those skilled in the art. In use, the motor 61 rotates the input shaft 63 which rotates the driving gear 62 which, in turn, rotates the driven gear 72 and the carrier member 50.

In other forms, the transfer member 71 may comprise any mechanism known to those skilled in the art by which rotational energy may be conducted from one shaft to another such as, for example, v-belts, timing belts, continuous chains and the like or combinations thereof. Further, the transfer member 71 may comprise any mechanism known to those skilled in the art by which input velocity can be variably modified to an output source such as, for example, cams, linkages, and the like or combinations thereof as long as the changes in rotational speed are substantially created by the motor 61.

It will be further appreciated that the transfer apparatuses 20 of the present disclosure may utilize one or, in the alternative, two, or three or more combinations of carrier members 50 (having any number of housings 51, such as two, three, or four), transfer members 71, and motors 61 in series to achieve the desired application of the article to the second moving carrier 80. The different combinations may allow the use of a continuously moving web or substrate to supply the discrete articles. In addition, greater speed ratio differential may be achieved by using combinations of transferring devices, driven mechanisms, driving mechanisms and motors in series.

Figure 3:
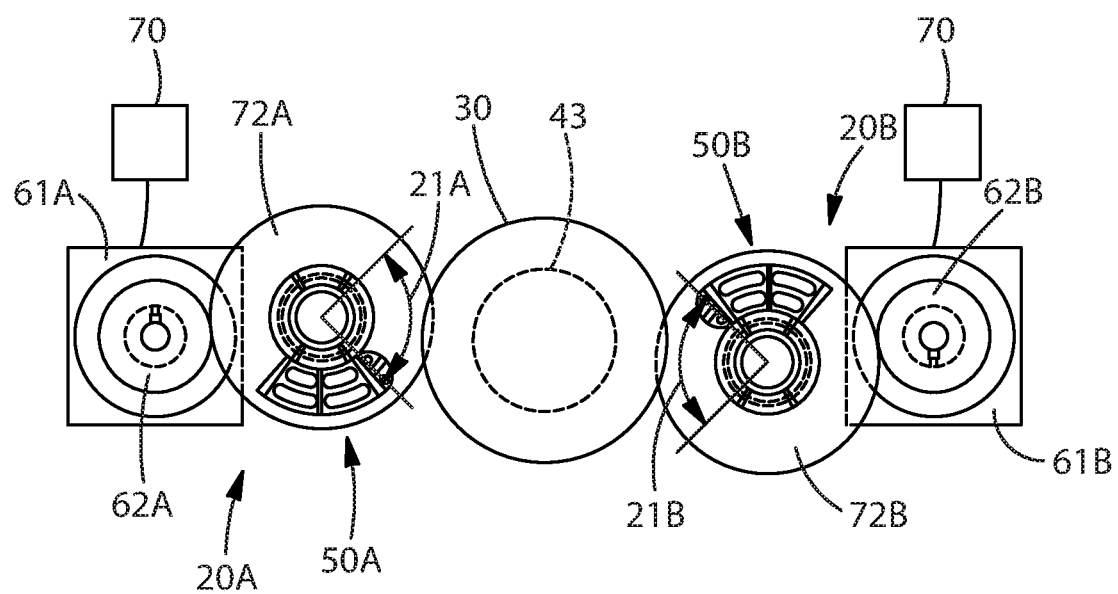
FIG. 3 is a schematic side view of two transfer apparatuses being used together in accordance with the present disclosure.

It will be further appreciated that the transfer apparatuses 20 of the present disclosure, when used in series, do not need to operate at the same receiving zone 21 and application zone 23. For example, referring to FIG. 3, there is representatively shown a transfer apparatus 20A comprising a carrier member 50A connected to a motor 61A by a driving gear 62A and driven gear 72A and a second transfer apparatus 20B comprising a carrier member 50B connected to a motor 61B by a driving gear 62B and a driven gear 72B. The transfer apparatus 20A uses a receiving zone 21A to accept articles 30 from a drum 43, while the transfer apparatus 20B uses a receiving zone 21B to accept articles 30 from the same drum 43 at a different rotational position on the drum.

Figure 4:
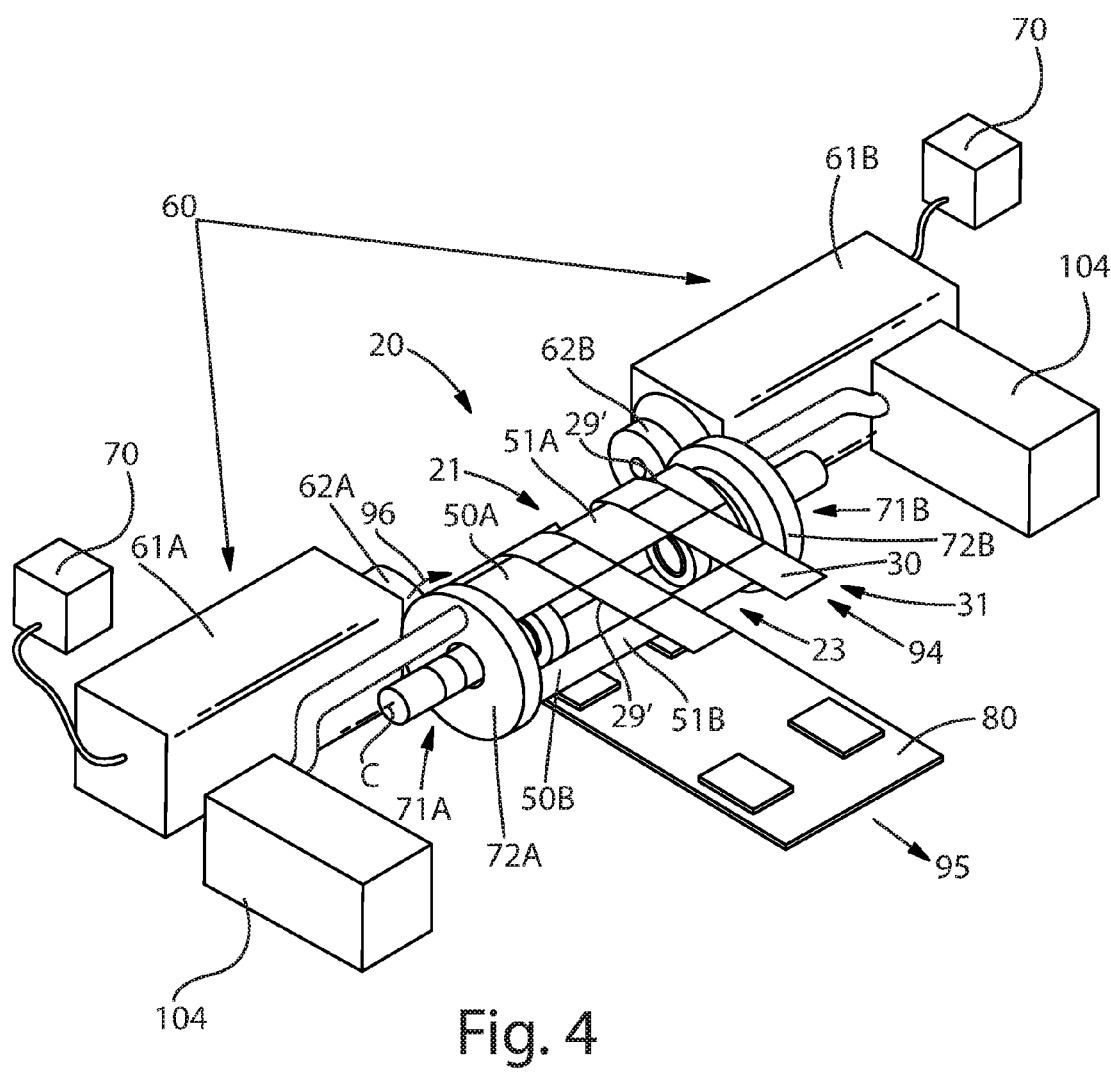
FIG. 4 is a perspective view of an example form comprising two transfer apparatuses used to transfer one or more articles from a first carrier moving at a first speed to a second carrier moving at a second speed in accordance with the present disclosure.

Another aspect of the present disclosure is illustrated, for example, in FIG. 4. A transfer apparatus 20 for receiving discrete articles 30 of a web of a material 31 traveling at a first speed in the direction indicated by arrow 94 is illustrated. The transfer apparatus 20 applies the articles 30 to the second moving carrier 80 traveling at a second speed in the direction indicated by arrow 95. The illustrated example of the transfer apparatus 20 comprises two rotatable carrier members, represented by 50A and 50B, for receiving and applying the articles 30. The transfer apparatus 20 may comprise a driving system 60 having two motors 61A and 61B, each of which may comprise a driving gear 62A, 62B for transmitting rotational energy to the transfer members 71A, 71B represented by the driven gears 72A, 72B.

As illustrated in FIG. 4, each carrier member 50A and 50B may comprise a housing 51A, 51B connected to or formed with the driven gear 72A, 72B. In some forms, the housings may be connected to the driven gears using adhesive bonding or gluing. As each of the driven gears 72A, 72B rotate, the carrier members 50A, 50B travel in the direction indicated by arrow 96. In use, the circumferential, outer peripheral surface of the housings 51A, 51B travel along and define an orbital path that passes through the receiving zone 21 and the application zone 23 defined by the respective regions of the orbital path traveled by the housings 51A, 51B of the carrier members 50A and 50B. The first and second transfer members 71A, 71B are generally aligned with respect to a common axis, C. The first and second carrier members 50A and 50B may be at least partially located between the first and second motors 61A, 61B. The first and second transfer members 71A, 71B, may also be at least partially located between the first and second motors 61A, 61B.

The size and shape of the housings 51A and 51B may vary as the number of housings per transfer apparatus changes. For example, if the machine includes two transfer apparatuses as representatively illustrated in FIG. 4, each of the housings 51A and 51B may have an outer peripheral arc length which spans from about 5 to about 175 degrees of the orbital path of the carrier members 50A and 50B.

Each transfer member 71A, 71B may comprise any mechanism known to those skilled in the art by which rotational energy may be conducted from one shaft to another such as, for example, v-belts, timing belts, continuous chains and the like or combinations thereof. Further, the transfer members 71A, 71B may comprise any mechanism known to those skilled in the art by which input velocity can be variably modified to an output source such as, for example, cams, linkages, and the like or combinations thereof as long as the changes in rotational speed are substantially created by the motor 61.

For receiving the articles in the receiving zone 21, the carrier member, as representatively illustrated in the various configurations, may comprise a gripping mechanism so that the outer concave surface of the housing may capture an article in the receiving zone 21 and transport the article to the application zone 23. In such an instance, the gripping mechanism may comprise a fluid pressure (e.g., vacuum) that may be selectively imposed through fluid ports in the housing leading to the outer surface of the housing. For instance, the fluid pressure may be activated in the receiving zone 21 to seize the articles and deactivated in the application zone 23 to release the articles to the second moving carrier 80. In other instances, a negative fluid pressure (i.e., vacuum) may be activated in the receiving zone 21 to seize the articles and a positive fluid pressure may be activated in the application zone 23 to "blow off" the articles onto the second moving carrier 80. In this manner, control may be maintained over the articles at all times during the transfer process between the receiving and application zones. Alternatively, the gripping mechanism may comprise any technique known to those skilled in the art for gripping and releasing articles such as, mechanical clamps, electrical clamps, magnetic clamps and the like or combinations thereof.

For transferring the articles 30 to the second moving carrier 80 in the application zone 23, the transfer apparatus 20 may comprise any of a variety of options known to those skilled in the art such as, adhesive applied on the article, adhesive applied on the moving carrier, an electrostatic charge between the article and moving carrier, vacuum on the moving carrier and the like or combinations thereof. In a form, the transfer may comprise the generation of a weld between the article and the carrier by any of a variety of means known to those skilled in the art such as, pressure generation at a nip formed between the housing and the moving carrier at transfer, interaction between a pattern on the housing and an ultrasonic horn behind the moving carrier at transfer, and the like, or combinations thereof. In addition, in order to aid the welding process, the part may be modified on the housing by energy addition using any mechanism known to those skilled in the art such as, for example, hot air currents, ultraviolet lighting, laser bombardment and the like, or combinations thereof.

The motor may comprise a programmable motor, such as a programmable rotary motor or a programmable linear motor. In other instances, a programmable rotary motor may be used on one transfer apparatus and a programmable linear motor may be used on another transfer apparatus. In still other instances, two programmable rotary motors may be used on two different transfer apparatuses or two programmable linear motors may be used on two different transfer apparatuses. The use of a programmable motor in the transfer apparatus may provide an inexpensive and adaptable method for receiving the articles 30 from the first moving carrier 29 traveling at a first speed and applying the articles 30 to the second moving carrier 80 traveling at a second different speed. The variable angular velocity of the carrier member may be produced by varying the current supplied to the motor. Since the transfer member is operably coupled to the output of the motor, changes in the angular velocity and position of the motor may directly correlate to changes in the angular velocity and position of the carrier member. The current supplied to the motor may be controlled using any of a variety of methods for programming motors known to those skilled in the art such as, standard cam curve functions, a reference data table containing reference points, desired motor encoder points, and the like or combinations thereof.

The programmable motors used to drive the carrier members may provide variable angular velocities including periods where the velocity remains constant for a fixed duration. These constant velocity dwell times may be advantageous in the receiving zone 21 and the application zone 23 particularly when the pick-up and transfer occurs over substantial arc lengths of contact. Alternatively, one or more of the constant speed regions may be changed to a controlled variable speed region. This may enable the article 30 to be picked up in the receiving zone 21 at a variable speed, which, when the part 30 is elastic, would allow tensions to be varied incrementally therein which may be desirous in certain product features. In another example, the constant speed of the motor 61 in the application zone 23 may be such that the corresponding speed of the carrier member is different from speed of the second moving carrier 80 at transfer. Such speed variations generate tension in the article 30 by incrementally transferring the article 30 in a controlled manner from one moving carrier traveling at one surface speed to a second moving carrier traveling at a second surface speed.

It will be further appreciated that the velocity of the carrier member 50 outside of the application zone 23 or the receiving zone 21 may be tailored to aid the performance of secondary processes including adhesive application, printing of identification or registration marks, application of bonding aids, moisture addition and the like and combinations thereof. Such changes in velocity may be beneficial by presenting specific velocity profiles or even additional periods of constant velocity, which may allow for more precise interaction with the secondary processes being performed.

Programmable motors may be purchased from any number of suppliers of programmable motors such as Rockwell Automation, located in Milwaukee, Wis. Further, the program inputs to the motors can be generated by one of ordinary skill in the art if provided with the analytical representation of the desired output function. For instance, the creation of the electronic cam profile for the motor may be developed by first determining the key input variables. The key input variables are based on desired product features, the base design of the transfer apparatus 20 and the desired cycle speed of the transfer apparatus 20. Secondly, the radius of the outer surface of the carrier member 50 is determined. Once the radius is determined, the required cam inputs of rotational velocities, distances traveled and time available for acceleration may be calculated, which serve as the input to the cam profile generator. Additional details regarding these calculations are disclosed, for example, in U.S. Pat. No. 6,450,321 to Blumenthal et al.

Figure 5:
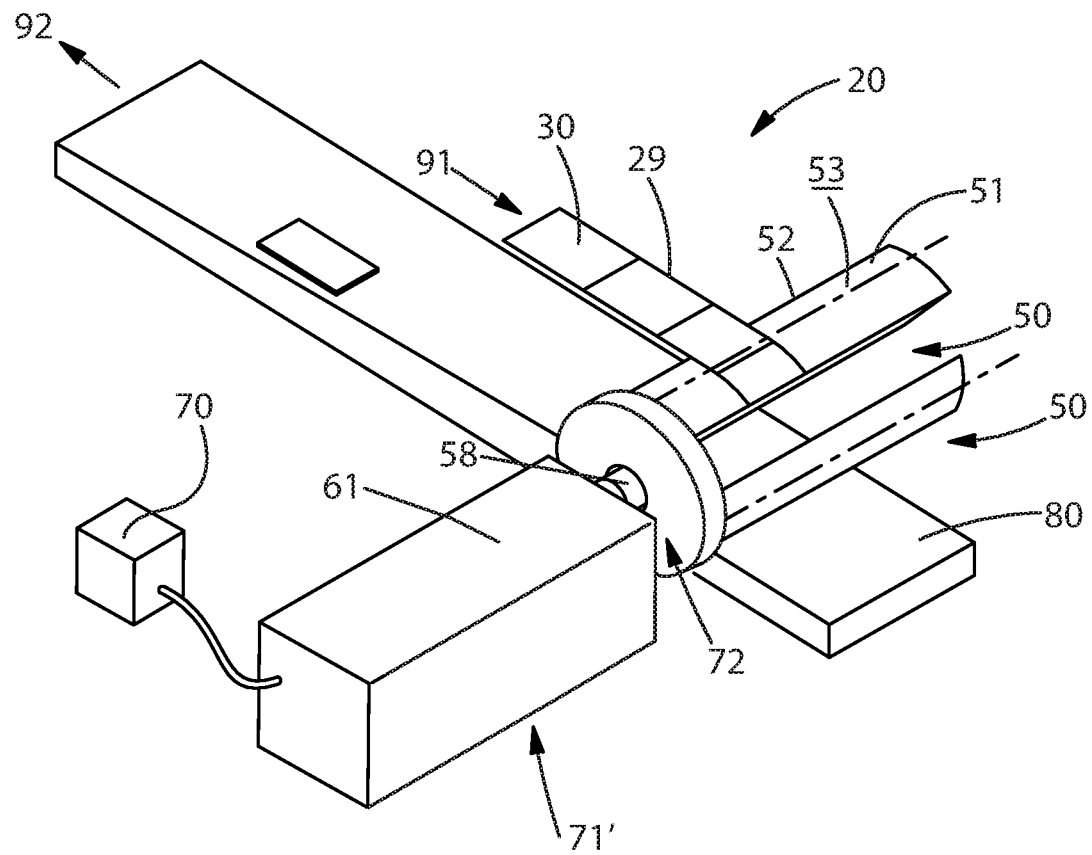
FIG. 5 is a perspective view of an example transfer apparatus used to transfer one or more articles from a first carrier moving at a first speed to a second carrier moving at a second speed in accordance with the present disclosure.
Figure 6:
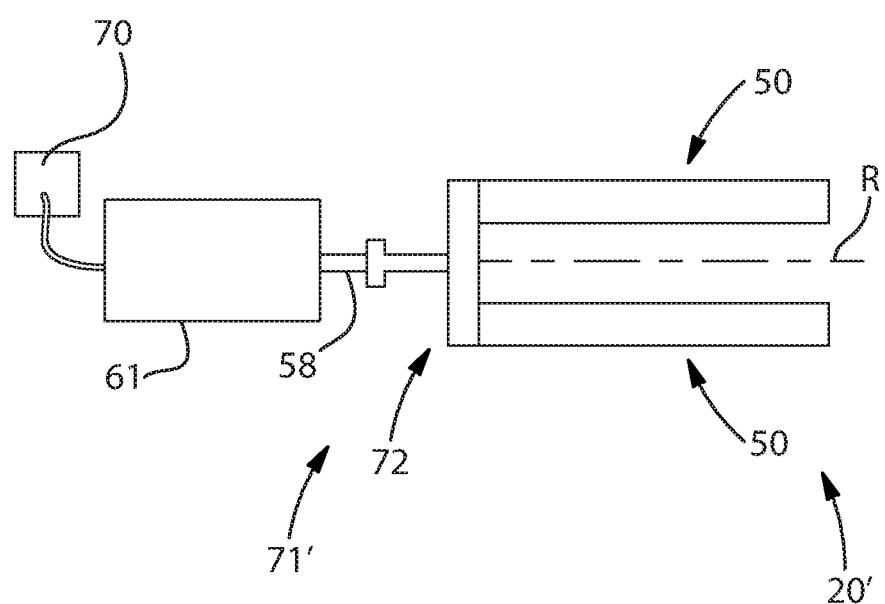
FIG. 6 is a side view of the transfer apparatus of FIG. 5, in accordance with the present disclosure.

Referring to FIGS. 5 and 6, an example form of the transfer apparatus of the present disclosure is illustrated. The transfer apparatus 20' may comprise one or more carrier members 50 engaged with or formed with a transfer member 72, and a motor or programmable motor 61. The transfer member 72 may be directly engaged with a drive shaft 58 of the motor or programmable motor 61. This is known as direct drive. Thus, the transfer member 72 is directly driven by the drive shaft 58 of the programmable motor 61. Stated another way, when the drive shaft 58 is rotated, the transfer member 72 is rotated about an axis of rotation, R. The carrier members 50, owing their engagement with the transfer member 72, are then are orbited about the axis of rotation, R. In some instances, another transfer apparatus (not illustrated), similar to the transfer apparatus 20' may be provided on an opposite side of the second moving carrier 80. In such an instance, a first carrier member may be operably engaged with or directly engaged with a first transfer member which is operably engaged with or directly engaged with a first programmable motor, wherein the first programmable motor is configured to rotate the first carrier member in an orbital path, and wherein the first transfer member is configured to guide the first carrier member in the orbital path. A second carrier member may be operably engaged with or directly engaged with a second transfer member which is operably engaged with or directly engaged with a second programmable motor, wherein the second programmable motor is configured to rotated the first carrier member in the orbital path, and wherein the second transfer member is configured to guide the second carrier member in the orbital path. The first and second carrier members and optionally the first and second transfer members may be at least partially, or fully, located between the first and second programmable motors. In other instances, the transfer members may not be provided and the carrier members may be directly engaged with the drive shafts of the programmable motors.

Figure 7:
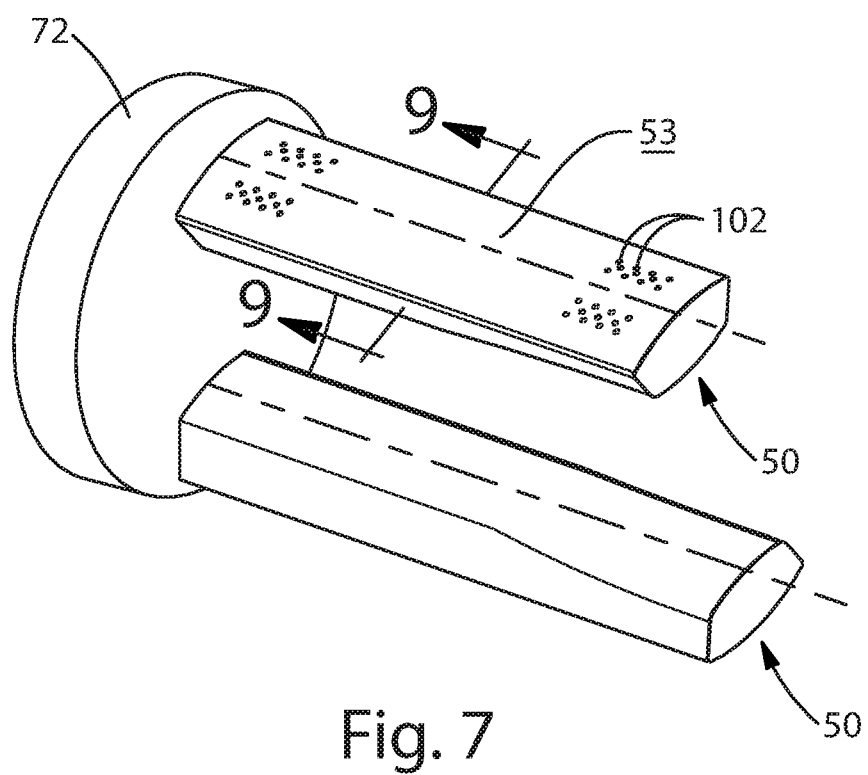
FIG. 7 is a perspective view of an example carrier member in accordance with the present disclosure.
Figure 8:
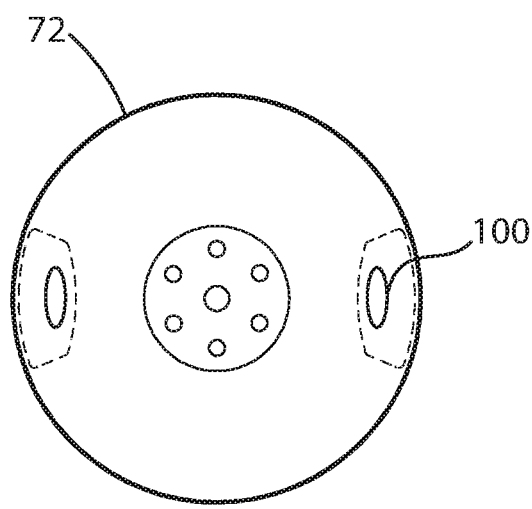
FIG. 8 is a rear view of the example carrier member of FIG. 7, in accordance with the present disclosure.

Referring to FIGS. 7 and 8, the carrier members 50 may each define one or more fluid cavities 100 therein. The outer surface 53 may define one or more fluid ports 102 therein. The one or more fluid ports 102 may be in fluid communication with the one or more fluid cavities 100 so that fluid pressure (positive and/or negative) may be applied to articles 30 positioned on the outer surface 53 of the carrier members in locations where the articles 30 overlap the one or more fluid ports 102. The one or more fluid cavities 100 may be in fluid communication with one or more fluid pumps (see e.g., fluid pump 104 in FIG. 1) configured to provide a positive and/or negative fluid pressure to the fluid cavities 100. In a form, one fluid pump may be configured to provide a positive fluid pressure and another fluid pump may be configured to provide a negative fluid pressure. One or more of the fluid pumps may be in fluid communication with a manifold (not illustrated) which is in fluid communication with at least some of the fluid cavities 100. In such an instance, positive and/or negative fluid pressure may be provided by the manifold to the at least some fluid cavities 100 as desired and as will be recognized by those of skill in the art.

As discussed above, the carrier members 50 of the present disclosure may comprise a housing 51 comprising a wall 52 and an outer surface 53, wherein at least a portion of the outer surface 53 may be configured to engage one or more articles 30 to be transferred. The wall, or portions thereof, may comprise carbon fiber. Other portions of the carrier member 50 or the housing 51 may also comprise carbon fiber. In addition, the transfer members may comprise carbon fiber. In certain instances, the transfer member may comprise carbon fiber and the wall 52 and/or the outer surface 53 may comprise aluminum, titanium, and/or other high-strength, low weight materials. In other instances, portions of the carrier members 50 may comprise carbon fiber, while other portions may comprise aluminum, titanium, and/or other high strength, low weight materials.

Figure 9:
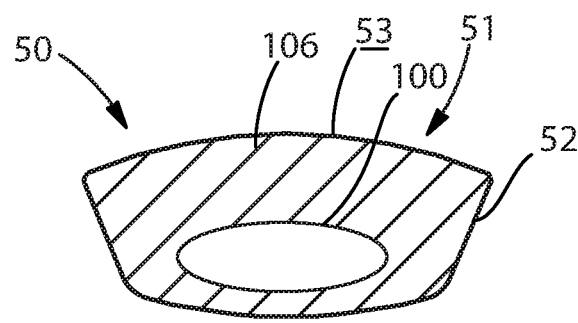
FIG. 9 is a cross-sectional view of a portion of the carrier member taken about line 9-9 of FIG. 7, in accordance with the present disclosure.

Referring to FIG. 9, an example cross-sectional view of the carrier member 50 taken about line 9-9 of FIG. 7 is illustrated. The wall 52 forms the perimeter, or at least portion of the perimeter of the housing 51. A fluid cavity 100 is formed within the housing 51 and, in places on the carrier member 50, is in fluid communication with the fluid ports 102 (see FIG. 7). The wall 52 may comprise one or more layers of carbon fiber, as will be discussed in further detail below. A support material 106 may be positioned within the housing 51. The one or more layers of carbon fiber of the wall 52 may be at least partially formed around or on the support material 106. Alternatively, the one or more layers of carbon fiber of the wall 52 may be formed first and then the support material 106 may be placed into a void created by the formed wall. In such an instance, the support material 106 may be pre-formed and then inserted into the void and/or may be injected into the void. The support material 106 may also at least partially surrounds the fluid cavity 100. The support material 106 may comprise a low density material, a low density foam, a plastic material, a non-foam material, or a foam material, for example.

Each programmable motor may be in electrical communication with a motor control system. The motor control system may comprise an amplifier and/or a controller. Example motor control systems 70 are illustrated in FIGS. 1-6. The motor control system 70 may regulate, control, and/or vary the speed at which the programmable motor runs throughout an orbit, or partial orbit, of the carrier member 50 causing the carrier member 50 to increase or decrease in speed based on where it is in its rotation (e.g., in the receiving zone 21, in the application zone 23, between the application zone 23 and a receiving zone 21, or between the receiving zone 21 and the application zone 23). Each pair of a motor control system and a programmable motor may define one or more excitation frequencies. The motor control system and the programmable motor may comprise a position loop, a velocity loop, and a current loop. Each of these loops may have an excitation frequency. Each of these excitation frequencies of the various loops may be different. When any of these excitation frequencies coincides with one or more natural frequencies of a carrier member comprising a wall (or other components) comprising carbon fiber, the carbon fiber tends to crack. As a result, carbon fiber has not previously been able to be used in the formation of portions of carrier members driven by a programmable motor in electrical communication with a motor control system. The present disclosure provides a solution to that problem by shifting the one or more natural frequencies of the carrier member comprising the carbon fiber outside of coincidence with the one or more excitation frequencies of the motor control system 70 and the programmable motor 61. The shifting of the one more natural frequencies of the carrier member may comprise certain layering of the carbon fiber, as will be described in further detail below.

In one instance, the one or more natural frequencies of the carrier member are each different than the one or more excitation frequencies of the motor control system and the programmable motor. In another instance, the one or more natural frequencies of the carrier member may be at least about 1.05 times greater than or at least about 1.05 times less than the one or more excitation frequencies of the motor control system and the programmable motor. In still another instance, the one or more natural frequencies of the carrier member may be at least about 1.1 times greater than or at least about 1.1 times less than the one or more excitation frequencies of the motor control system and the programmable motor. In still another instance, the one or more natural frequencies of the carrier member may be at least about 2 times greater than or at least about 2 times less than the one or more excitation frequencies of the motor control system and the programmable motor The one or more natural frequencies of the carrier member may also be about 1.1 times to about 10 times, about 2 times to about 10 times, or about 1.2 to about 5 times greater than or less than the one or more excitation frequencies of the motor control system and the programmable motor. All 0.01 increments within the above-specified ranges and all ranges formed therein or thereby are specifically recited herein, but not written out for brevity. This non-coincidence of the one or more natural frequencies of the carrier member with the one or more excitation frequencies of the motor control system and the programmable motor allows carbon fibers to be used as a component (e.g., as a wall) of the carrier members without cracking, or substantial cracking.

In an instance, where the motor control system and the programmable motor have a first excitation frequency for the position loop, a second excitation frequency for the velocity loop, and a third excitation frequency for the current loop, the one or more natural frequencies of the carrier member may be at least 1.1 times, at least 1.2 times, at least 2 or more times, greater than or less than all of the first, second, and third excitation frequencies of the various loop. The ranges specified in the above-paragraph also apply here, including the 0.01 increments statement.

The one or more natural frequencies of the carrier member may have a torsional frequency, a flexural frequency and an axial frequency. Each of the torsional frequency, the flexural frequency, and the axial frequency may be at least 1.05 times, at least 1.1 times, at least 1.2 times, or at least 2 or more times greater than or less than each of the excitation frequencies of each of the position, velocity, and current loops of the motor control system and the programmable motor to at least inhibit coincidence between the one or more natural frequencies and the one or more excitation frequencies. The ranges specified two paragraphs above also apply here, including the 0.01 increments statement.

By eliminating coincidence with the one or more natural frequencies of the carrier member comprising carbon fiber and the one or more excitation frequencies of the motor control system and the programmable motor, carbon fiber may now be used in the construction of carrier members without cracking, or without substantial cracking, thereby allowing for carrier members that have high strength and very light weight.

Figure 10:
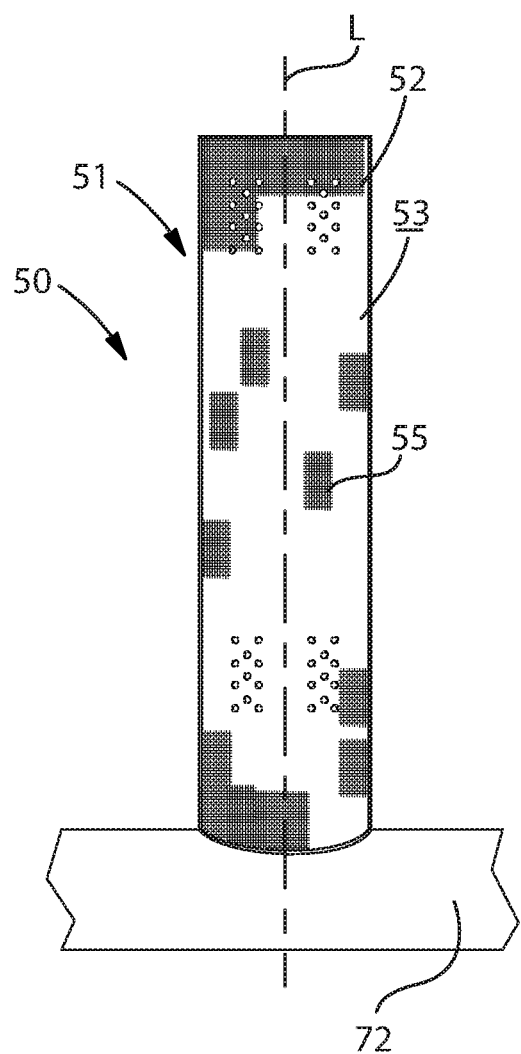
FIG. 10 is a top view of the carrier member of FIG. 7, in accordance with the present disclosure.

To shift the one or more natural frequencies of a carrier member comprising a wall comprising carbon fiber, various carbon fiber layering techniques may be used. Referring to FIG. 10, a top view of the carrier member of FIG. 7 is illustrated. The carrier member 50 comprises a longitudinal axis, L. The outer surface 53 of the wall 52 of the housing 51 of the carrier member 50 may comprise a woven carbon fiber material 55. The woven carbon fiber material 55 may comprise a first carbon fiber material having a first carbon fiber orientation extending generally parallel to the longitudinal axis, L and may comprise a second carbon fiber material extending generally perpendicular to the longitudinal axis, L. In other instances, the first and second carbon fiber orientations may be about 90 degrees from each other, but may not be parallel and perpendicular, respectively, to the longitudinal axis, L. In other forms, the first and second carbon fiber orientations may be any other suitable angle relative to each other and relative to the longitudinal axis, L, as long as the one or more natural frequencies of the carrier member is shifted appropriately away from coincidence with the one or more excitation frequencies of the motor control system and the programmable motor. In other instances the carbon fiber material 55 may be a uniaxial, non-woven material or other non-woven material.

Figure 11:
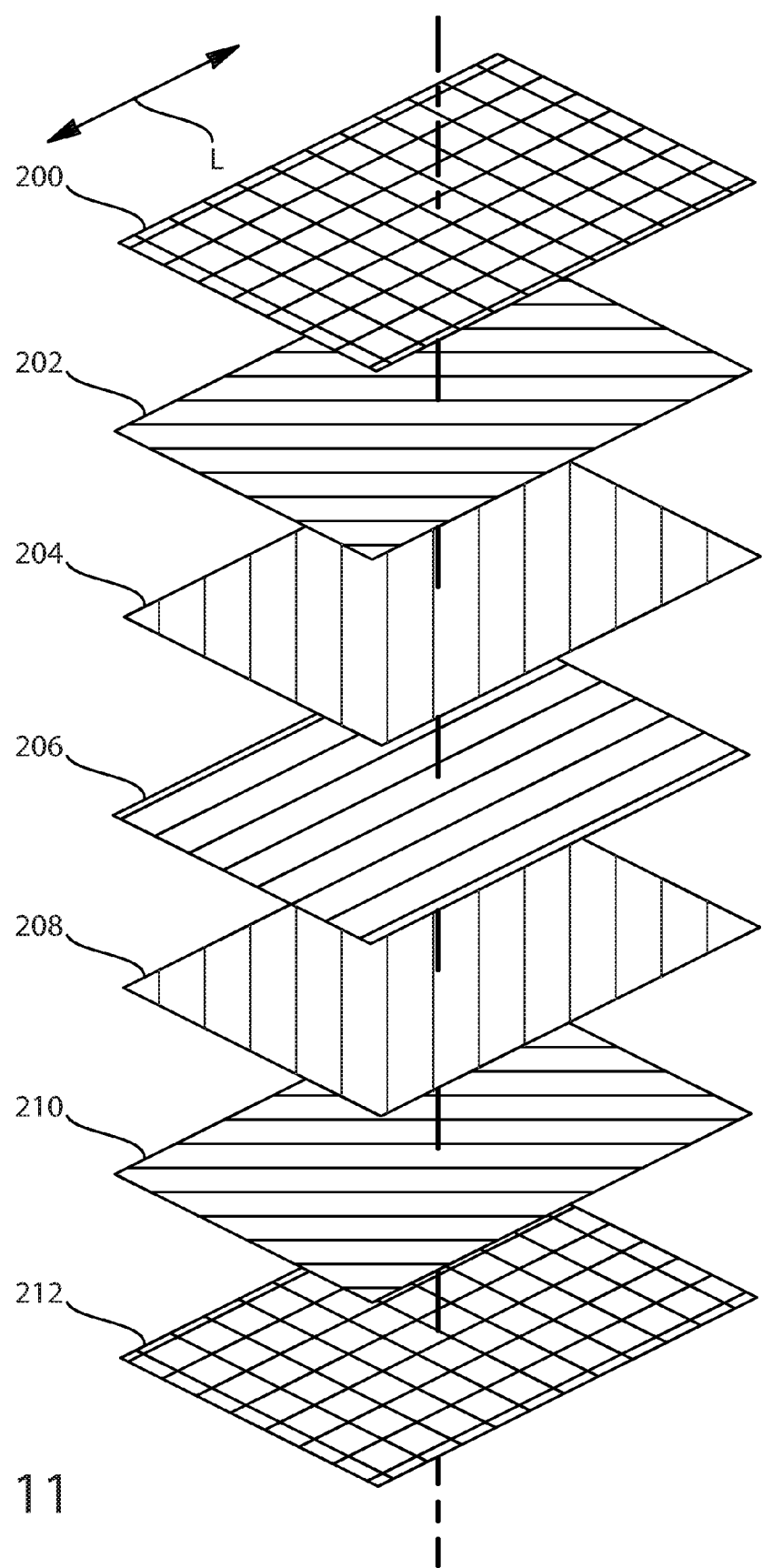
FIG. 11 illustrates example layering of carbon fiber in accordance with the present disclosure.

Referring to FIG. 11, a plurality of carbon fiber layers that may form at least a portion of the wall 52 of the housing 51 of the carrier member 50 are illustrated as an example. The longitudinal axis, L, of the carrier member 50 of FIG. 10 is provided for reference in FIG. 11. The first layer 200 may comprise a woven carbon fiber material, a uniaxial carbon fiber material, or other non-woven carbon fiber material. The first layer 200 may form at least a portion of the outer surface 53 of the carrier member 50. The second layer 202 may comprise carbon fiber having a carbon fiber orientation extending in the range of about 50 degrees to about 10 degrees, about 40 degrees to about 20 degrees, about 35 degrees to about 25 degrees, about 30 degrees to about 20 degrees, about 35 degrees, about 30 degrees, about 25 degrees, or about 20 degrees, relative to the longitudinal axis, L, specifically reciting all 0.1 degree increments within the above-referenced ranges and all ranges formed therein or thereby. The third layer 204 may comprise carbon fiber having a carbon fiber orientation extending in the range of about −50 degrees to about −10 degrees, about −40 degrees to about −20 degrees, about −35 degrees to about −25 degrees, about −30 degrees to about −20 degrees, about −35 degrees, about −30 degrees, about −25 degrees, or about −20 degrees, relative to the longitudinal axis, L, specifically reciting all 0.1 degree increments within the above-referenced ranges and all ranges formed therein or thereby. The fourth layer 206 may comprise carbon fiber having a carbon fiber orientation that is parallel to, or substantially parallel to (e.g., +/−5 degrees), the longitudinal axis, L. The fifth layer 208 may comprise carbon fiber having a carbon fiber orientation extending in the range of about −50 degrees to about −10 degrees, about −40 degrees to about −20 degrees, about −35 degrees to about −25 degrees, about −30 degrees to about −20 degrees, about −35 degrees, about −30 degrees, about −25 degrees, or about −20 degrees, relative to the longitudinal axis, L, specifically reciting all 0.1 degree increments within the above-referenced ranges and all ranges formed therein or thereby. The sixth layer 210 may comprise carbon fiber having a carbon fiber orientation extending in the range of about 50 degrees to about 10 degrees, about 40 degrees to about 20 degrees, about 35 degrees to about 25 degrees, about 30 degrees to about 20 degrees, about 35 degrees, about 30 degrees, about 25 degrees, or about 20 degrees, relative to the longitudinal axis, L, specifically reciting all 0.1 degree increments within the above-referenced ranges and all ranges formed therein or thereby. The seventh layer 212 may comprise a woven carbon fiber material, a uniaxial carbon fiber material, or other non-woven carbon fiber material. The seventh layer may form 212 at least a portion of the inner surface of the wall 52 of the carrier member 50. The carbon fiber material of the seventh layer 212 may be the same as or different than the carbon fiber material of the first layer 200. In some instances, the seventh layer 212 may be in contact with or at least partially surround the support material 106. The layers 200-212 may be laid down in order from the seventh layer 212 to the first layer 200 or vice versa.

Figure 12:
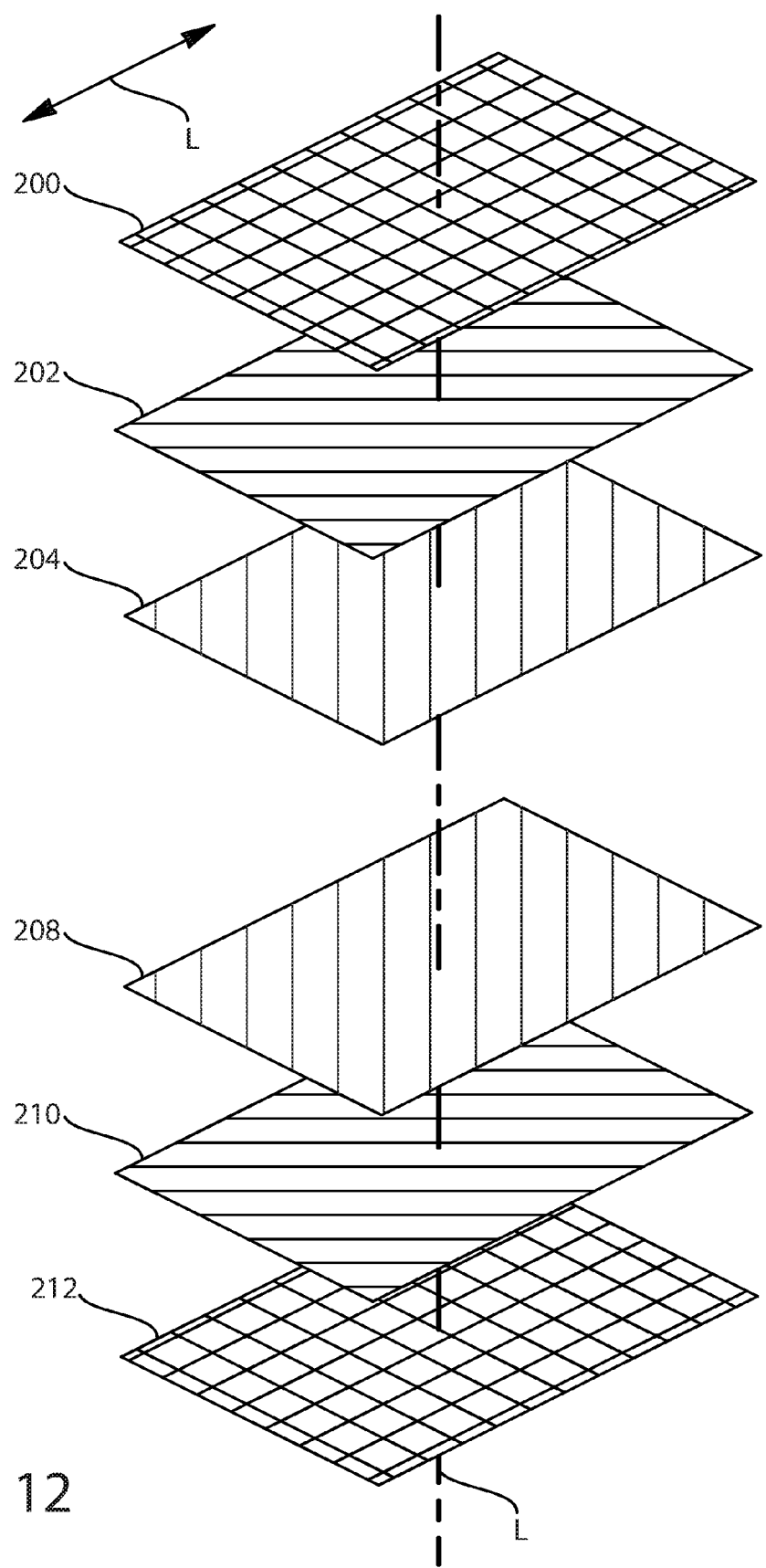
FIG. 12 illustrates example layering of carbon fiber in accordance with the present disclosure.

Referring to FIG. 12, the layering is the same as FIG. 11, with the exception of the fourth layer 206 being eliminated. The longitudinal axis, L, of the carrier member 50 of FIG. 10 is provided for reference in FIG. 12.

Figure 13:
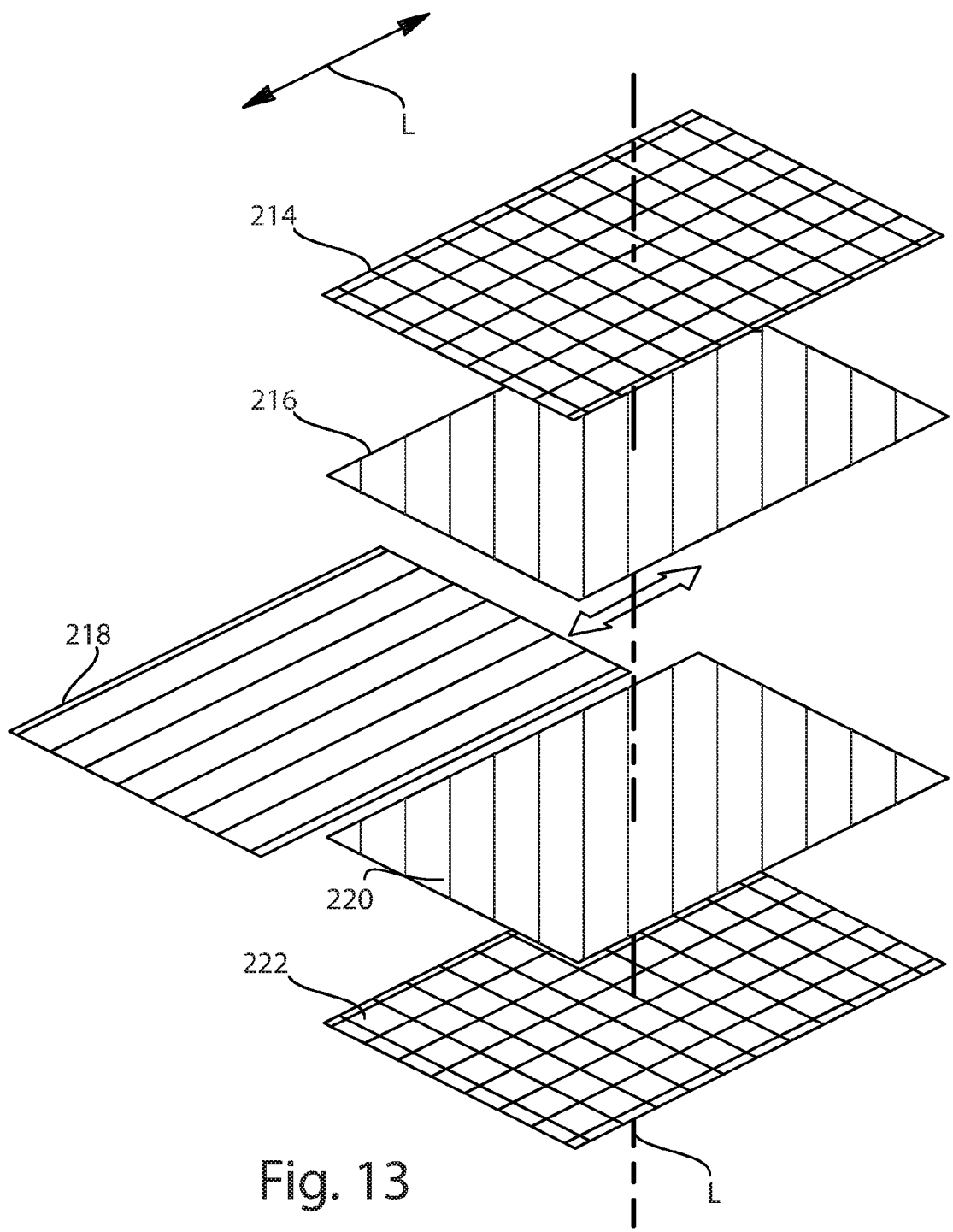
FIG. 13 illustrates example layering of carbon fiber in accordance with the present disclosure.

Referring to FIG. 13, a plurality of carbon fiber layers that may form at least a portion of the wall 52 of the housing 51 of the carrier member 50 are illustrated as an example. The longitudinal axis, L, of the carrier member 50 of FIG. 10 is provided for reference in FIG. 13. The first layer 214 may comprise a woven carbon fiber material, a uniaxial carbon fiber material, or a non-woven carbon fiber material. The first layer 214 may forms at least a portion of the outer surface 53 of the carrier member 50. The second layer 216 may comprise carbon fiber having a carbon fiber orientation extending in the range of about −50 degrees to about −10 degrees, about −40 degrees to about −20 degrees, about −35 degrees to about −25 degrees, about −30 degrees to about −20 degrees, about −35 degrees, about −30 degrees, about −25 degrees, or about −20 degrees, relative to the longitudinal axis, L, specifically reciting all 0.1 degree increments within the above-referenced ranges and all ranges formed therein or thereby. The third layer 218 is optional and if provided may comprise carbon fiber having a carbon fiber orientation that is parallel to, or substantially parallel to (e.g., +/−5 degrees), the longitudinal axis, L. The fourth layer 220 may comprise carbon fiber having a carbon fiber orientation extending in the range of about −50 degrees to about −10 degrees, about −40 degrees to about −20 degrees, about −35 degrees to about −25 degrees, about −30 degrees to about −20 degrees, about −35 degrees, about −30 degrees, about −25 degrees, or about −20 degrees, relative to the longitudinal axis, L, specifically reciting all 0.1 degree increments within the above-referenced ranges and all ranges formed therein or thereby. The fifth layer 222 may comprise a woven carbon fiber material, a uniaxial carbon fiber material, or a non-woven carbon fiber material. The carbon fiber material of the fifth layer 222 may be the same as or different than the carbon fiber material of the first layer 214. The fifth layer may form 222 at least a portion of the inner surface of the wall 52 of the carrier member 50. In some instances, the fifth layer 222 may be in contact with or at least partially surround the support material 106. The layers 214-222 may be laid down in order from the fifth layer 222 to the first layer 214 or vice versa.

Figure 14:
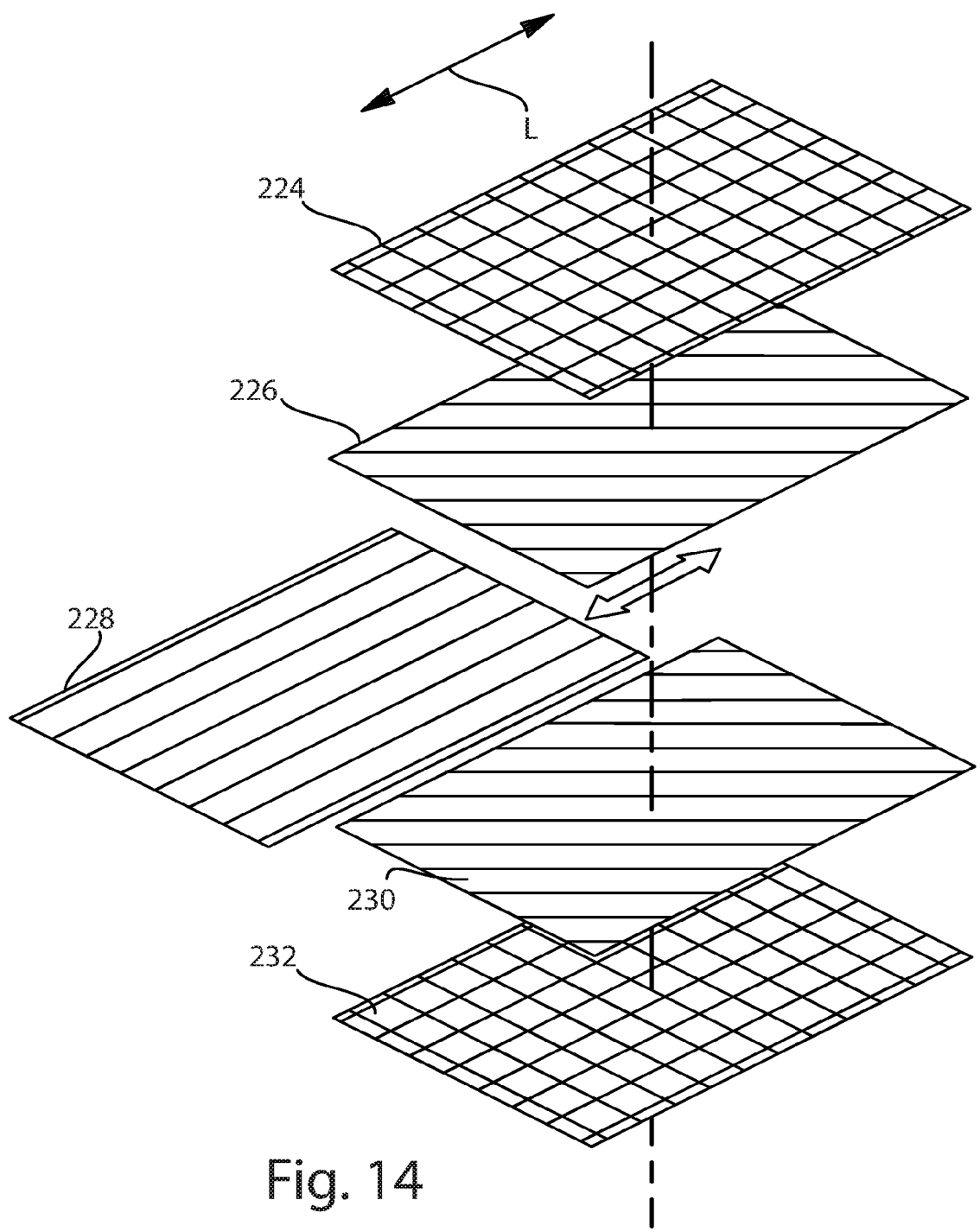
FIG. 14 illustrates example layering of carbon fiber in accordance with the present disclosure.

Referring to FIG. 14, a plurality of carbon fiber layers that may comprise at least a portion of the wall 52 of the housing 51 of the carrier member 50 are illustrated as an example. The longitudinal axis, L, of the carrier member 50 of FIG. 10 is provided for reference in FIG. 14. The first layer 224 may comprise a woven carbon fiber material, a uniaxial carbon fiber material, or a non-woven carbon fiber material. The first layer 224 may form at least a portion of the outer surface 53 of the carrier member 50. The second layer 226 may comprise carbon fiber having a carbon fiber orientation extending in the range of about 50 degrees to about 10 degrees, about 40 degrees to about 20 degrees, about 35 degrees to about 25 degrees, about 30 degrees to about 20 degrees, about 35 degrees, about 30 degrees, about 25 degrees, or about 20 degrees, relative to the longitudinal axis, L, specifically reciting all 0.1 degree increments within the above-referenced ranges and all ranges formed therein or thereby. The third layer 228 is optional and if provided may comprise carbon fiber having a carbon fiber orientation that is parallel to, or substantially parallel to (e.g., +/−5 degrees), the longitudinal axis, L. The fourth layer 230 may comprise carbon fiber having a carbon fiber orientation extending in the range of about 50 degrees to about 10 degrees, about 40 degrees to about 20 degrees, about 35 degrees to about 25 degrees, about 30 degrees to about 20 degrees, about 35 degrees, about 30 degrees, about 25 degrees, or about 20 degrees, relative to the longitudinal axis, L, specifically reciting all 0.1 degree increments within the above-referenced ranges and all ranges formed therein or thereby. The fifth layer 232 may comprise a woven carbon fiber material, a uniaxial carbon fiber material, or a non-woven carbon fiber material. The carbon fiber material of the fifth layer 232 may be the same as or different than the carbon fiber material of the first layer 224. The fifth layer may form 232 at least a portion of the inner surface of the wall 52 of the carrier member 50. In some instances, the fifth layer 232 may be in contact with or at least partially surround the support material 106. The layers 224-232 may be laid down in order from the fifth layer 232 to the first layer 224 or vice versa.

Figure 15:
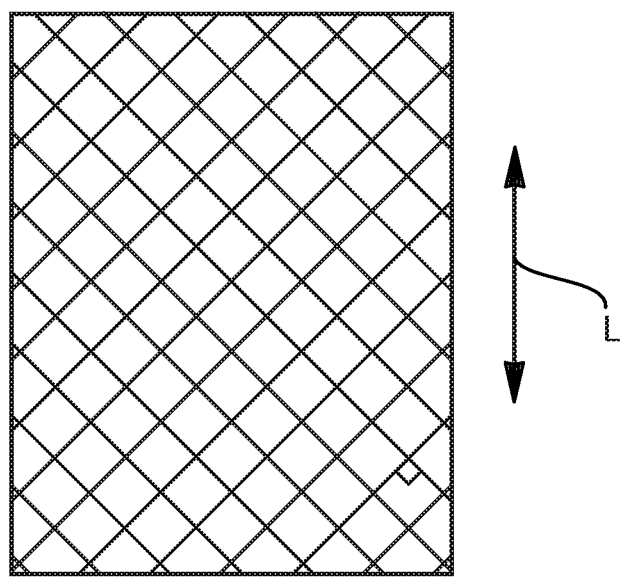
FIG. 15 illustrates an example woven carbon fiber pattern in accordance with the present disclosure.

Referring to FIG. 15, a woven carbon fiber material is illustrated as an example. In this instance, the woven carbon fiber material comprises a first carbon fiber material having a first carbon fiber orientation extending about 45 degrees from the longitudinal axis, L, of the carrier member 50 (see e.g., FIG. 10) and having a second carbon fiber material having a second carbon fiber orientation extending about 45 degrees from the longitudinal axis, L, of the carrier member 50. Other orientations relative of the first and second carbon fiber materials, relative to the longitudinal axis, are also within the scope of the present disclosure.

As referenced above, carbon fiber materials having uniaxial carbon fiber orientations may be used as at least a portion of the outer surface 53 of the wall 52. The uniaxial carbon fiber orientation may extend in a direction parallel, or substantially parallel, to the longitudinal axis, L, of the carrier members 50 (see e.g., FIG. 10). In other instances, the uniaxial carbon fiber orientation may extend in a direction perpendicular to, substantially perpendicular to, or transverse to the longitudinal axis, L, of the carrier members.

As will be recognized from the carbon fiber layering examples disclosed herein, one important aspect is to have symmetry with respect to the middle of a carbon fiber wall or with respect to a middle layer of a carbon fiber wall if an odd number of layers are provided. This symmetry provides the carbon fiber with strength.

A resin or other suitable material may be used intermediate the various layers to hold the layers together. Other known carbon fiber layer joining techniques may also be used. Any of the outer surfaces of the housings may comprise a plasma coating to modify the interaction of the outer surfaces with the article being transferred, such as providing for a higher or lower coefficient of friction, providing for better glue release, and/or providing for better traction control. Other coatings, such as Nickel, may be used to accomplish the same function or a similar function.

In one form, a method of manufacturing a transfer assembly configured to transfer one or more articles from a first moving carrier to a second moving carrier is provided. The method comprises providing a programmable motor and a motor control system for the programmable motor, wherein the motor control system and the programmable motor define one or more excitation frequencies. The method comprises providing a carrier member comprising a housing comprising a wall or carbon fiber portion and shifting a natural frequency of the carrier member by forming the wall or the carbon fiber portion with a first carbon fiber layer having a first fiber orientation extending in a first direction and with a second carbon fiber layer having a second fiber orientation extending in a second direction that is different than the first direction. The shifting the natural frequency step establishes the natural frequency of the carrier member to be at least 1.1 times greater than (including the other values and ranges expressed herein) or at least 1.1 times less than (including the other values and ranges expressed herein) the excitation frequency of the motor control system and the programmable motor.

The housing comprises a longitudinal axis (see L, in FIGS. 7 and 10). The first direction of the first fiber orientation may be in the range of −40 to −20 degrees (including the other values and ranges expressed herein) from the longitudinal axis. The second direction of the second fiber orientation may be in the range of +20 to +40 degrees (including the other values and ranges expressed herein) from the longitudinal axis. The first and second directions may generally oppose each other relative to the longitudinal axis L.

As described above, the motor control system and the programmable motor may have an excitation frequency in each of the position loop, the velocity loop, and the current loop. The shifting the natural frequency step establishes the one or more natural frequencies of the carrier member to be at least 1.1 times greater than (including the other values and ranges expressed herein) or at least 1.1 times less than (including the other values and ranges expressed herein) each of the excitation frequencies of the position loop, the velocity loop, and the current loop.

As described above, the one or more natural frequencies may comprise a torsional frequency, a flexural frequency, and an axial frequency. Each of the torsional, flexural, and axial frequencies may be at least 1.1 times greater than (including the other values and ranges expressed herein) or at least 1.1 times less than (including the other values and ranges expressed herein) each of the excitation frequencies of the position loop, the velocity loop, and the current loop.

In one form, a method of shifting a natural frequency of a carrier member comprising a housing comprising a wall or other carbon fiber portion (e.g., any portion of the carrier member) is provided. The carrier member is configured to be rotated about an axis of rotation by a programmable motor in communication with a motor control system such that the carrier member is configured to transfer one or more articles from a first moving carrier to a second moving carrier. The motor control system and the programmable motor may have a plurality of excitation frequencies. The method may comprises forming the wall (or other portion of the housing or carrier member) of the housing of the carrier member, wherein the forming step comprises placing a first carbon fiber layer having a first fiber orientation extending in a first direction and placing a second carbon fiber layer on a first side of the first layer. The second carbon fiber layer may have a second fiber orientation extending in a second direction that is different than the first direction. The forming step further comprises placing a third carbon fiber layer on a second side of the first layer. The third carbon fiber layer may have a third fiber orientation extending generally in the second direction such that the plurality of excitation frequencies of the motor control system and the programmable motor do not interfere with the natural frequency of the carrier member. The natural frequency of the carrier member may be at least 1.1 times greater than (including the other values and ranges expressed herein) or at least 1.1 times less than (including the other values and ranges expressed herein) each of the plurality of excitation frequencies. The forming the wall or other carbon fiber portion of the housing of the carrier member step may comprise placing a fourth carbon fiber layer on the second carbon fiber layer. The fourth carbon fiber layer may have a fourth fiber orientation extending in a third direction. The forming the wall of the housing of the carrier member may comprise placing a fifth carbon fiber layer on the third carbon fiber layer. The fifth carbon fiber layer may have a fifth fiber orientation extending generally in the third direction. The second direction may be generally opposite to the third direction. The forming the wall or other carbon fiber portion of the housing of the carrier member step may comprise placing a sixth layer of woven carbon fiber on the fourth layer and placing a seventh layer of woven carbon fiber on the fifth layer. The first direction may be different than the second and third directions. The forming the wall or other carbon fiber portion of the housing of the carrier member step may also comprise forming the wall or other carbon fiber portion such that the wall or other carbon fiber portion at least partially surrounds a support material or such that the wall or other carbon fiber portion contacts the support material.

In one form, a method of forming a wall (or other portion) of a housing of a carrier member is provided. The housing defines a longitudinal axis. The carrier member has a natural frequency that may be at least 1.1 times greater than (including the other values and ranges expressed herein) or at least 1.1 times less than (including the other values and ranges expressed herein) an excitation frequency of a programmable and a motor control system for the programmable motor. The carrier member is configured to transfer one or more articles from a first moving carrier to a second moving carrier. The programmable motor is configured to rotate the carrier member about an axis of rotation. The method comprises applying a first carbon fiber layer, wherein the first carbon fiber layer may have a first fiber orientation extending in the range of −40 to −20 degrees from the longitudinal axis, and applying a second carbon fiber layer, wherein the second carbon fiber layer may have a second fiber orientation extending in the range of −40 to −20 degrees from the longitudinal axis. The first and second carbon fiber layers may together form the wall, or a portion thereof.

The method may further comprise applying a third carbon fiber layer positioned intermediate the first and second carbon fiber layers. The third carbon fiber layer may have a third fiber orientation extending in a direction that is generally parallel to the longitudinal axis. The first, second, and third carbon fiber layers may together form the wall, or a portion thereof.

Alternatively, the method may further comprise applying a third carbon fiber layer to the first carbon fiber layer, wherein the third carbon fiber layer may have a third fiber orientation extending in the range of +20 to +40 degrees from the longitudinal axis and applying a fourth carbon fiber layer to the second carbon fiber layer, wherein the fourth carbon fiber layer may have a fourth fiber orientation extending in the range of +20 to +40 degrees from the longitudinal axis. The first, second, third, and fourth carbon fibers layers may together form the wall, or a portion thereof.

Again alternatively, the method may further comprise applying a third layer of woven carbon fiber to the first carbon fiber layer or to the second carbon fiber layer, wherein the third layer of woven carbon fiber may comprise a first carbon fiber material having a carbon fiber orientation extending generally parallel to the longitudinal axis and a second carbon fiber material extending generally perpendicular to the longitudinal axis, and wherein the first, second, and third layers may together form the wall, or a portion thereof.

Again alternatively, the method may further comprise applying a third layer of woven carbon fiber to the first carbon fiber layer or to the second carbon fiber layer, wherein the third layer of woven carbon fiber may comprise a first carbon fiber material having a third carbon fiber orientation and a second carbon fiber material having a fourth carbon fiber orientation extending generally perpendicular to the third carbon fiber orientation. The first, second, and third layers may together form the wall, or a portion thereof.

The method may further comprise applying a fifth layer of woven carbon fiber to the third carbon fiber layer or to the fourth carbon fiber layer (if the third and fourth carbon fibers layers are not woven carbon fiber materials). The first, second, third, fourth, and fifth fiber layers may together form the wall, or a portion thereof.

In one instances, more than one woven carbon fiber layer may be provided on the outer surface or within the wall.

In a form, the present disclosure may use a component, formed at least partially of carbon fiber, in any portion of an absorbent article manufacturing or processing line or manufacturing or processing line for any other product or intermediate product (hereafter absorbent article processing line). In a form, the present disclosure may use a component, formed at least partially of carbon fiber, in a portion of a piece of equipment of an absorbent article processing line. In a form, the present disclosure may use a component, formed at least partially of carbon fiber, in a transfer apparatus of an absorbent article processing line. In a form, the present disclosure may use a component, formed at least partially of carbon fiber, in a transfer head of a transfer apparatus of an absorbent article processing line. The various components, formed at least partially of carbon fiber, discussed above may be manufactured such that their natural frequency is shifted at least 1.1 times greater than or at least 1.1 times less than (or other ranges specified herein) various excitation frequencies emitted by equipment and/or control systems of an absorbent article processing line. The various components, formed at least partially of carbon fiber, are desirable in view of them being high strength, low weight, and durable materials that may be used during high speed movements (e.g., accelerations, decelerations) for achieving high throughput in absorbent article processing lines.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any embodiment disclosed or claimed herein or that it alone, or in any combination with any other reference or references, teaches, suggests or discloses any such embodiment. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications may be made without departing from the spirit and scope of the present disclosure. It is therefore intended to cover in the appended claims all such changes and modifications that are within the scope of this disclosure.

What is claimed is:

1. A method of manufacturing a transfer assembly configured to transfer one or more articles from a first moving carrier to a second moving carrier, the method comprising:
    providing a programmable motor;
    providing a motor control system for the programmable motor, wherein the motor control system and the programmable motor define an excitation frequency;
    providing a carrier member comprising a housing comprising a carbon fiber portion; and
    shifting a natural frequency of the carrier member by forming the carbon fiber portion with a first carbon fiber layer having a first fiber orientation extending in a first direction and with a second carbon fiber layer having a second fiber orientation extending in a second direction that is different than the first direction, wherein the shifting the natural frequency step establishes the natural frequency of the carrier member to be at least 1.1 times greater than or at least 1.1 times less than the excitation frequency of the motor control system and the programmable motor.

2. The method of claim 1, wherein the housing comprises a longitudinal axis, wherein the first direction is in the range of −40 to −20 degrees from the longitudinal axis, and wherein the second direction is in the range of +20 to +40 degrees from the longitudinal axis, and wherein the first and second directions generally oppose each other relative to the longitudinal axis.

3. The method of claim 1, wherein the shifting the natural frequency step establishes the natural frequency of the carrier member to be at least two times greater than or at least two times less than the excitation frequency of the motor control system and the programmable motor.

4. The method of claim 1, wherein the motor control system and the programmable motor have an excitation frequency in each of a position loop, a velocity loop, and a current loop, wherein the shifting the natural frequency step establishes the natural frequency of the carrier member to be at least 1.1 times greater than or at least 1.1 times less than each of the excitation frequencies of the position loop, the velocity loop, and the current loop.

5. The method of claim 4, wherein the natural frequency comprises a torsional frequency, a flexural frequency, and an axial frequency, and wherein each of the torsional, flexural, and axial frequencies are at least 1.1 times greater than or at least 1.1 times less than each of the excitation frequencies of the position loop, the velocity loop, and the current loop.

6. The method of claim 1, wherein the carbon fiber portion comprises a wall, and wherein the wall at least partially surrounds a support material.

7. The method of claim 6, wherein the support material comprises foam.

8. The method of claim 6, wherein the wall contacts the support material.

9. The method of claim 1, wherein the motor control system and the programmable motor have an excitation frequency in each of a position loop, a velocity loop, and a current loop, wherein the shifting the natural frequency step establishes the natural frequency of the carrier member to be at least 2 times greater than or at least 2 times less than each of the excitation frequencies of the position loop, the velocity loop, and the current loop.

10. The method of claim 1, wherein the natural frequency comprises a torsional frequency, a flexural frequency, and an axial frequency, and wherein each of the torsional, flexural, and axial frequencies are at least 2 times greater than or at least 2 times less than each of the excitation frequencies of the position loop, the velocity loop, and the current loop.

11. The method of claim 1, wherein the programmable motor comprises a programmable linear motor.

12. The method of claim 1, wherein the programmable motor comprises a programmable rotary motor.

13. The method of claim 1, comprising providing a plasma coating on an outer portion of the carrier member.

14. The method of claim 1, comprising providing a woven carbon fiber material as a portion of the carbon fiber portion.

15. The method of claim 1, comprising providing a transfer member operably engaged with the programmable motor and the carrier member.

16. A method of manufacturing a transfer assembly configured to transfer one or more articles from a first moving carrier to a second moving carrier, the method comprising:
    providing a programmable motor;
    providing a motor control system for the programmable motor, wherein the motor control system and the programmable motor define an excitation frequency;
    providing a carrier member comprising a housing comprising a carbon fiber portion; and
    shifting a natural frequency of the carrier member by forming the carbon fiber portion with a first carbon fiber layer having a first fiber orientation extending in a first direction and with a second carbon fiber layer having a second fiber orientation extending in a second direction that is different than the first direction, wherein the shifting the natural frequency step establishes the natural frequency of the carrier member to be at least 1.2 times greater than or at least 1.2 times less than the excitation frequency of the motor control system and the programmable motor.

17. The method of claim 16, wherein the housing comprises a longitudinal axis, wherein the first direction is in the range of −40 to −20 degrees from the longitudinal axis, and wherein the second direction is in the range of +20 to +40 degrees from the longitudinal axis, wherein the first and second directions generally oppose each other relative to the longitudinal axis, wherein the carbon fiber portion comprises a wall, and wherein the wall at least partially surrounds a support material.

18. A method of manufacturing a transfer assembly configured to transfer one or more articles from a first moving carrier to a second moving carrier, the method comprising:
    providing a programmable motor;

providing a motor control system for the programmable motor, wherein the motor control system and the programmable motor define an excitation frequency;

providing a carrier member comprising a housing comprising a carbon fiber portion; and shifting a natural frequency of the carrier member by forming the carbon fiber portion with a first carbon fiber layer having a first fiber orientation extending in a first direction and with a second carbon fiber layer having a second fiber orientation extending in a second direction that is different than the first direction, wherein the shifting the natural frequency step establishes the natural frequency of the carrier member to be 2 to 10 times greater than or 2 to 10 times less than the excitation frequency of the motor control system and the programmable motor.

19. The method of claim 18, wherein the motor control system and the programmable motor have an excitation frequency in each of a position loop, a velocity loop, and a current loop, wherein the shifting the natural frequency step establishes the natural frequency of the carrier member to be 2 to 10 times greater than or 2 to 10 times less than each of the excitation frequencies of the position loop, the velocity loop, and the current loop.

20. The method of claim 19, wherein the natural frequency comprises a torsional frequency, a flexural frequency, and an axial frequency, and wherein each of the torsional, flexural, and axial frequencies are 2 to 10 times greater than or 2 to 10 times less than each of the excitation frequencies of the position loop, the velocity loop, and the current loop.

* * * * *